United States Patent
Colomb et al.

(10) Patent No.: US 8,640,695 B2
(45) Date of Patent: Feb. 4, 2014

(54) DEVICE FOR DISPENSING A FLUID PRODUCT

(75) Inventors: Arnaud Colomb, Verneuil sur Seine (FR); Zakaria Sallak, Rouen (FR)

(73) Assignee: Aptar France SAS, Le Neubourg (FR)

( * ) Notice: Subject to any disclaimer, the term of this patent is extended or adjusted under 35 U.S.C. 154(b) by 327 days.

(21) Appl. No.: 12/988,475

(22) PCT Filed: Apr. 10, 2009

(86) PCT No.: PCT/FR2009/050645
§ 371 (c)(1),
(2), (4) Date: Oct. 18, 2010

(87) PCT Pub. No.: WO2009/136098
PCT Pub. Date: Nov. 12, 2009

(65) Prior Publication Data
US 2011/0036349 A1    Feb. 17, 2011

(30) Foreign Application Priority Data

Apr. 16, 2008   (FR) ...................................... 08 52546

(51) Int. Cl.
*A61M 15/00*   (2006.01)
(52) U.S. Cl.
USPC ................................................... 128/203.15
(58) Field of Classification Search
USPC ........................... 128/200.11–200.24, 203.12
See application file for complete search history.

(56) References Cited

U.S. PATENT DOCUMENTS

| 6,012,454 | A | 1/2000 | Hodson et al. | |
| 2008/0142008 | A1* | 6/2008 | Pocock et al. | 128/203.15 |
| 2009/0178677 | A1* | 7/2009 | Pocock et al. | 128/203.15 |

FOREIGN PATENT DOCUMENTS

| FR | 2 896 419 A1 | | 1/2006 |
| FR | 2 881 120 A1 | | 7/2006 |
| WO | WO 2006/079751 A1 | * | 8/2006 |
| WO | 2008/012458 A2 | | 1/2008 |

* cited by examiner

*Primary Examiner* — Loan Thanh
*Assistant Examiner* — Andrew S Lo
(74) *Attorney, Agent, or Firm* — Sughrue Mion, PLLC

(57) ABSTRACT

A fluid dispenser device including a body provided with a dispenser orifice; at least one reservoir containing a dose of fluid, such as pharmaceutical powder; a movable support mechanism that receives at least one reservoir, and that is displaceable between a non-dispensing position and a dispensing position. A reservoir-opening mechanism opens a reservoir when actuated and a stressing mechanism that includes an elastically-deformable stressing element, urges the movable support mechanism towards a dispensing position. An inhalation trigger releases a blocking element and which enables the movable support mechanism, together with a reservoir, to be displaced towards the dispensing position at the time a user inhales.

9 Claims, 2 Drawing Sheets

DEVICE FOR DISPENSING A FLUID PRODUCT

CROSS REFERENCE TO RELATED APPLICATIONS

This application is a National Stage of International Application No. PCT/FR2009/050645 filed Apr. 10, 2009, claiming priority based on French Patent Application No. 08 52546 filed Apr. 16, 2008, the contents of all of which are incorporated herein by reference in their entirety.

FIELD OF THE INVENTION

The present invention relates to a fluid dispenser device, and more particularly to a dry-powder inhaler.

BACKGROUND OF THE INVENTION

Dry-powder inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Another type of inhaler consists in packaging the doses of powder in individual pre-dosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk.

Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. Obviously however, the inhaler is more difficult to use, since the user is obliged to load a capsule into the inhaler before each use.

All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers.

A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multi-dose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. In a variant, it has been proposed to perforate the closure layer or wall. That can present the drawback that the cut wall-portions risk retaining a fraction of the dose inside the reservoir, so that metering accuracy and reproducibility are therefore not guaranteed.

Documents FR-2 881 120, WO 2008/012458, U.S. Pat. No. 6,012,454, and FR-2 896 419 describe prior-art devices.

BRIEF SUMMARY OF THE INVENTION

An object of the present invention is to provide a fluid dispenser device, in particular a dry-powder inhaler, that does not have the above-mentioned drawbacks.

In particular, an object of the present invention is to provide a device that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide a device that avoids any risk of under-dosing, with the reservoir being opened, the dose being expelled, and the emitted dose being counted only in the event of the user inhaling. In addition, an object of the present invention is to avoid any risk of doses being lost in the absence of any inhalation, even if the user manipulates the device.

The present invention thus provides a fluid dispenser device comprising: a body provided with a dispenser orifice; at least one reservoir containing a dose of fluid, such as pharmaceutical powder; movable support means that receive at least one reservoir, and that are displaceable between a non-dispensing position and a dispensing position; reservoir-opening means for opening a reservoir when said opening means are actuated; stressing means for urging said movable support means towards said dispensing position, said stressing means including an elastically-deformable stressing element; blocking means for retaining said movable support means in the non-dispensing position corresponding to a cocked position of said blocking means; and inhalation trigger means for releasing said blocking means and for enabling said movable support means, together with a reservoir, to be displaced towards said dispensing position at the time a user inhales; the device including means for modifying the inhalation flow of the user, which means, at the start of inhalation, are adapted to use the inhalation flow mainly to actuate said inhalation trigger means, and, at the end of inhalation, are adapted to use the inhalation flow mainly to expel the dose of fluid contained in the open reservoir.

Advantageously, said means for modifying the inhalation flow are adapted to increase the resistance to inhalation at the start of inhalation, and to decrease said resistance at the end of inhalation.

Advantageously, said means for modifying the inhalation flow are adapted to limit the inhalation flow rate at the start of inhalation, and to increase said rate at the end of inhalation.

Advantageously, said means for modifying the inhalation flow comprise a movable element that is deformable and/or displaceable between a plugging position in which it plugs an inhalation air passage, and an unplugging position in which it does not plug said passage, said movable element being in its plugging position when the movable support means are in the non-dispensing position, and in its unplugging position when the movable support means are in the dispensing position.

Advantageously, said air passage is formed in said body and is connected to an inhalation endpiece, said movable element co-operating firstly with said body and secondly with said movable support means.

Advantageously, said movable element is pivotally mounted relative to said body.

Advantageously, said movable element is elastically deformable relative to said body.

Advantageously, said movable element includes at least two branches that are connected to a pivot-forming central zone, a first branch co-operating with the movable support means, and a second branch co-operating with said air passage.

Advantageously, said movable element includes a third branch that is adapted to bear and/or to slide against a portion that is fixed relative to said body.

Advantageously, said blocking means comprise a blocking element that is movable between a blocking position and an unblocking position, said blocking element co-operating with a projection that is secured to movable support means, said blocking element including a substantially plane bearing surface against which said projection of rounded shape comes to bear, displacement of said blocking element towards its unblocking position causing said projection to slide towards an end edge of said bearing surface, from which position the movable support means are displaced towards their dispensing position by said stressing means, the contact point in the cocked position between the projection and the bearing surface being situated at a non-zero distance from said end edge.

Advantageously, said blocking element is pivotally mounted on the body.

Advantageously, the force exerted by the stressing means on said movable support means in the cocked position lies in the range 5 newtons (N) to 10 N.

Advantageously, the force generated by inhalation of the patient sufficient to release said blocking means lies in the range 0.05 N to 0.2 N.

Advantageously, the inhalation rate of the patient that is sufficient to release said blocking means lies in the range 10 liters per minute (L/min) to 20 L/min.

Advantageously, the pressure difference created during inhalation that is sufficient to release said blocking means lies in the range 4 millibars (mbar) to 15 mbar.

Advantageously, the ratio between the force exerted by the stressing means on said movable support means in the cocked position and the force generated by inhalation of the user that is sufficient to release said blocking means lies in the range 80 to 120, in particular about 100.

Advantageously, said elastically-deformable stressing element comprises a compressible spring.

Advantageously, said blocking means comprise a rod that is connected at one end to means that are deformed under the effect of inhalation, and that is connected at its other end to the blocking element.

Advantageously, the device includes at least one cover element that is movable between a closed position and an open position, the displacement of said at least one movable cover element towards its open position bringing said device into its cocked position.

Advantageously, said inhalation trigger means comprise a flexible pouch.

Advantageously, the device includes a plurality of individual reservoirs disposed one behind another on an elongate flexible strip.

Advantageously, said reservoir-opening means comprise a perforator needle that is stationary relative to the body.

BRIEF DESCRIPTION OF THE DRAWINGS

These and other characteristics and advantages of the present invention appear more clearly from the following detailed description of an embodiment thereof, given by way of non-limiting example, and with reference to the accompanying drawing, in which.

DETAILED DESCRIPTION OF THE INVENTION

Figure 1:
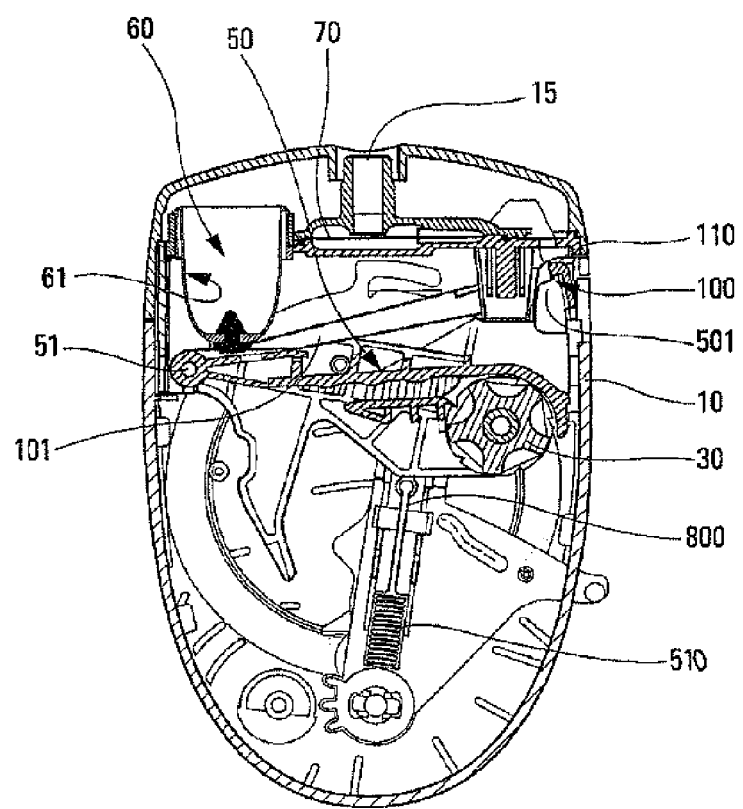
FIG. 1 is a diagrammatic view partially in section of a related art variant of a fluid dispenser device, in its cocked position, shown before inhalation.

The present invention preferably relates to a dry-powder inhaler. Only one embodiment is shown in the figures, and numerous other embodiments could naturally be used. The drawings are therefore non-limiting. In addition, numerous characteristics of the inhaler could thus be implemented in order to dispense liquid instead of powder. The inhaler comprises a central body 10 on which there are slidably or pivotably mounted two lateral elements or wings (not shown) that form a cover when the device is closed and that are adapted to be moved apart in order to open the device and thus cock the device. The body 10 can be generally rounded in shape in its bottom portion, and relatively flat in its top portion, as shown in the FIG. 1, but it could be of any other appropriate shape. The body 10 includes a dispenser and inhaler orifice 15 through which the user inhales while the device is being actuated, so as to create the inhalation flow.

A substrate of individual reservoirs (not shown) can be provided inside the body. The reservoirs are advantageously of the blister type, and the reservoir substrate is preferably a flexible elongate strip on which the blisters are disposed one behind another, in any appropriate number, in known manner. The blister strip may advantageously be constituted by a base layer or wall that forms cavities receiving the doses of powder, and by a closure layer or wall that covers each of said blisters in sealed manner. The blister strip can be rolled-up inside the body, and first displacement means 30 for displacing the strip are provided for progressively unrolling the blister strip and for bringing a respective blister or individual reservoir into a dispensing position each time the device is actuated. When an individual reservoir has been emptied by inhalation, the strip portion that includes said empty reservoirs is advantageously adapted to be rolled-up at another location of said body 10.

Reservoir-opening means 80 are provided in, or secured to, the body 10, the opening means comprising perforator and/or cutter means for perforating or cutting the closure layer of the blisters. The opening means are shown in diagrammatic manner only in the figures.

Movable support means 50 are adapted to support at least the reservoir that is to be opened during the next inhalation. The movable support means 50 forming second displacement means that are adapted to displace the reservoir to be emptied against said opening means of the device during actuation. Advantageously, the movable support means 50 are urged directly or indirectly by stressing means 800 comprising an elastically-deformable stressing element 51, such as a spring, a rod, or any other equivalent resilient element, said stressing element being prestressed in particular while the device is being opened. Advantageously, the movable support means 50 are displaceable between a first position (a non-dispensing position) and a second position (a dispensing position) that is the position for opening the reservoir and thus the inhalation position. The movable support means 50 are retained in the cocked position by appropriate blocking means 100 that are adapted to be triggered by inhalation, as explained below.

The movable support means 50 advantageously comprise a substantially rigid part, such as a rod, that is hinged or pivoted about a pin 51 relative to said body 10. A guide or indexer wheel 30 that is fastened in rotary manner on said movable support means 50 receives and guides the blisters. Turning the guide wheel 30 thus causes the blister strip to advance in a first direction. In a particular angular position, a given reservoir or blister is always in position to be opened by the opening means.

The indexer wheel 30 thus forms first displacement means for displacing the reservoirs, making it possible to cause the flexible strip to advance during each actuation cycle, whereas said movable support means 50 form second displacement means that bring a respective reservoir against said opening means 80 on each actuation.

While the reservoir is being displaced towards its opening position in order to be opened by the opening means 80, the opening means are preferably stationary relative to the body 10. However, it is possible to envisage that the opening means could also move during the step of opening the reservoir. For example, the opening means could be displaced towards the reservoir while the reservoir is being displaced towards the opening means. In another variant, it is also possible to envisage that the reservoir and the opening means are displaced in the same direction during actuation, the reservoir being displaced more quickly in said direction, such that it comes into contact with said opening means in order to be opened.

As explained above, it is desirable for the opening means to be actuated by the user inhaling. In order to trigger the reservoir-opening means by inhalation, an inhalation trigger system is provided that advantageously comprises means 60 that are displaceable and/or deformable under the effect of inhalation, the means 60 being adapted to release the blocking means 100. The means 60 advantageously comprises a deformable air-chamber or pouch 61 that co-operates with the blocking means 100 of said movable support means 50. Inhalation by the user causes said deformable air-chamber 61 to deform, thereby making it possible to release said blocking means 100 and therefore unblock the movable support means 50, so as to make it possible to displace the guide wheel 30, and thus the reservoir to be emptied, towards its opening position. Advantageously, the air chamber 61 can be connected firstly to the inhaler orifice 15, and secondly to said blocking means 100 in direct or indirect manner. Thus, during inhalation, the chamber 61 deforms and/or contracts, thereby causing said blocking means 100 to be displaced into an unblocking position. The air chamber 61 is connected to the inhaler orifice 15 via a channel that is advantageously disposed around a fluid expulsion channel that is itself connected to a dispenser chamber 70. The chamber 61 may be fastened to a rod 101 that is connected to the blocking means 100, inhalation causing the chamber 61 to deform thereby causing the rod 101 to pivot in order to displace said blocking means 100.

The inhaler further includes a dispenser chamber 70 for receiving the dose of powder after a respective reservoir has been opened. The dispenser chamber 70 is advantageously provided with at least one substantially spherical element, such as a bead (not shown), that is displaced inside said chamber 70 during inhalation so as to improve dispensing of the air and powder mixture after a reservoir has been opened, in order to increase the effectiveness of the device.

After inhalation, when the user closes the device, all of the components return to their initial, rest position, i.e. the movable support means 50 pivot about their pivot axis to return to their non-dispensing position by moving away from the reservoir-opening means, and the stressing element is also returned to its initial rest position in which it is not compressed or deformed. The device is thus ready for a new utilization cycle.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

As explained above, blocking means 100 are provided for retaining said movable support means 50 in said non-dispensing position, corresponding to a cocked position of the blocking means. Said blocking means 100 advantageously include a blocking element 110 that is adapted to co-operate with an extension or projection 501. When the projection is no longer retained, the movable support means 50 can be displaced towards their dispensing position under the effect of the force exerted thereon by the stressing means 800. Said blocking means 100 are advantageously connected by means of a rod 101 to the deformable chamber 61 that is sensitive to inhalation by the user, so that while the user inhales, said chamber deforms, thus causing the rod 101 to pivot, and consequently said blocking element 110, thereby releasing the extension 501. This enables said movable support means 50 to be displaced towards their dispensing position under the effect of the force exerted by the compressed spring 51. The displacement of the movable support means 50 causes an individual reservoir to be opened, as described above.

After inhalation, the blocking means 100 have pivoted, and the movable support means 50 have been displaced upwards by the compressed spring 51. The pivoting of the blocking means, in particular of the blocking element 110, may cause an end portion of the blocking element 110 to project out from the body 10, as shown in particular in FIG. 3. Then, when the user closes the movable cover elements, one of the cover elements, when fully closed, comes to bear against said end portion, thereby returning the blocking means 100 to their initial position with the chamber 61 that is also returned to its initial position.

Thus, by opening the inhaler, the user stresses the system. If the user does not inhale and closes the inhaler, said inhaler merely returns to its start position without displacing the reservoirs or the blocking means 100. There is thus no risk of a reservoir (and thus an active dose of substance) being lost by accidental or incomplete actuation in which the user does not inhale between opening and closing. Opening the reservoir, emptying it, dispensing the powder into the lungs of the user, and displacing the blister strip to bring a new full reservoir to face the opening means is thus possible only if the user inhales.

Thus, the blocking means need to be put under stress in order to be released. Prestressing is thus applied to the mechanism. The patient's inhalation causes the deformable chamber 61 to deform, thereby causing the blocking element 110 to turn and the mechanism to be released. An advantage of the blocking means is to be able to function with a ratio of 100 between applied prestressing and the force necessary to deform the diaphragm. A force in the range 0.05 newtons (N) to 0.2 N is generally sufficient to deform the diaphragm (which force is generated by patient inhaling) in spite of a prestressing force in the range 5 N to 10 N being applied to the mechanism (prestressing making it possible to guarantee a perforation force that is sufficient to enable the needle to penetrate into the blister. It suffices for the patient to generate a pressure difference lying in the range 4 millibars (mbar) to 15 mbar (pressure corresponding to inhalation at a rate lying in the range 10 liters per minute to 20 liters per minute) in order to trigger the mechanism: this inhalation rate is a rate that is considered to be comfortable for a patient who is asthmatic or who has a chronic respiratory tract disease. The rate being generated at the end of perforation enables the powder to be guided towards the patient's bronchi, while if the minimum inhalation rate is not achieved then no dose is released: this prevention device thus prevents the fluid dispenser device from being triggered accidentally.

Judicious sharing of the air flow makes it possible to guarantee the operation of the blocking means (½ to ⅔ of the overall flow), while also achieving the desired powder-dispensing performance (⅓ to ½ of the overall flow).

The blocking means can be re-cocked by the blocking element 110, or, in a variant, by a torsion spring, or even by the resilience of the chamber 61. Such re-cocking enables the mechanism to return to its initial state after each inhalation cycle as soon as the inhaler is closed, and in repeatable manner.

In advantageous manner, in the event of the device being opened and closed without any inhalation, the system remains at rest. There is therefore no risk of overdosing. In addition, no prestress is applied while the inhaler is not open, thereby favoring the stability of the components over time. Advantageously, when the inhaler is in the closed position, the projection 501 is disposed at a non-zero distance from the blocking element so as to ensure the system can be re-cocked.

In the invention, the device includes means for modifying the inhalation flow, which means are adapted to limit the inhalation flow at the start of inhalation, then to increase said inhalation flow at the end of inhalation. In the embodiment in FIGS. 2 and 3, these means comprise a movable element 700 that is deformable and/or displaceable between a plugging position (FIG. 2) and an unplugging position (FIG. 3). In its plugging position, the movable element 700 plugs or closes, via an extension 705, an air passage 75 that is advantageously formed in a portion of the body 10 that is connected to the inhalation endpiece. All or almost all of the inhalation flow is thus available for deforming the deformable chamber 61. However, in its unplugging position, the air passage 75 is no longer closed, thereby making it possible to reduce resistance to inhalation by the patient, thereby improving the comfort of the user. This also makes it possible to optimize the inhalation flow for expelling the dose of powder from the open reservoir. Before the reservoir is opened, the majority of the flow serves to trigger the system, and after opening, the majority of the flow serves to expel the dose. This also makes it possible to impart variable resistance to the inhalation trigger system.

Thus, by plugging the air passage 75 it is possible to anticipate the moment of triggering and to decrease the operating range of the blocking means. In other words, for a given change in trigger pressure or a given mechanical trigger force, the range of inhalation flow is reduced, thereby causing a temporary increase in the resistance, while increasing industrial substance. After opening the air passage, the flow may be increased so as to encourage good emptying of the open reservoir.

The movable element 700 is in its plugging position when the movable support means 50 are in the non-dispensing position, and in its unplugging position when the movable support means 50 are displaced into the dispensing position. Advantageously, the movable element 700 includes a portion, preferably a first branch 701, that co-operates with said movable support means 50, preferably with a projection 59 thereof, which portion is adapted to deform and/or displace another portion of the movable element 700, preferably a second branch 702, from its plugging position towards its unplugging position, as shown in FIG. 3. The first and second branches 701 and 702 are preferably connected to a pivot-forming central zone 704. The branches may be pivoting and/or elastically deformable about said zone 704, such that the movable element as a whole may be pivoting and/or elastically deformable relative to the body 10. Advantageously, a third branch 703 is connected to said central zone 704, which branch is adapted to co-operate, in particular to slide, over a portion that is fixed relative to the body 10, so as to provide guidance for the movable element and better stability for the system.

Figure 2:
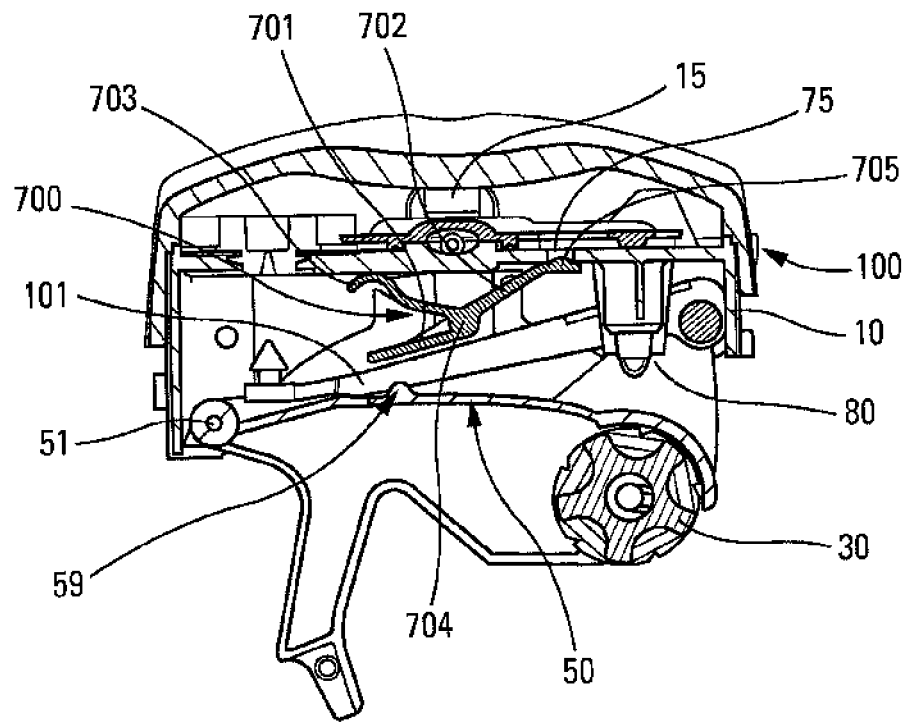
FIG. 2 shows an advantageous embodiment of the invention, before inhalation.
Figure 3:
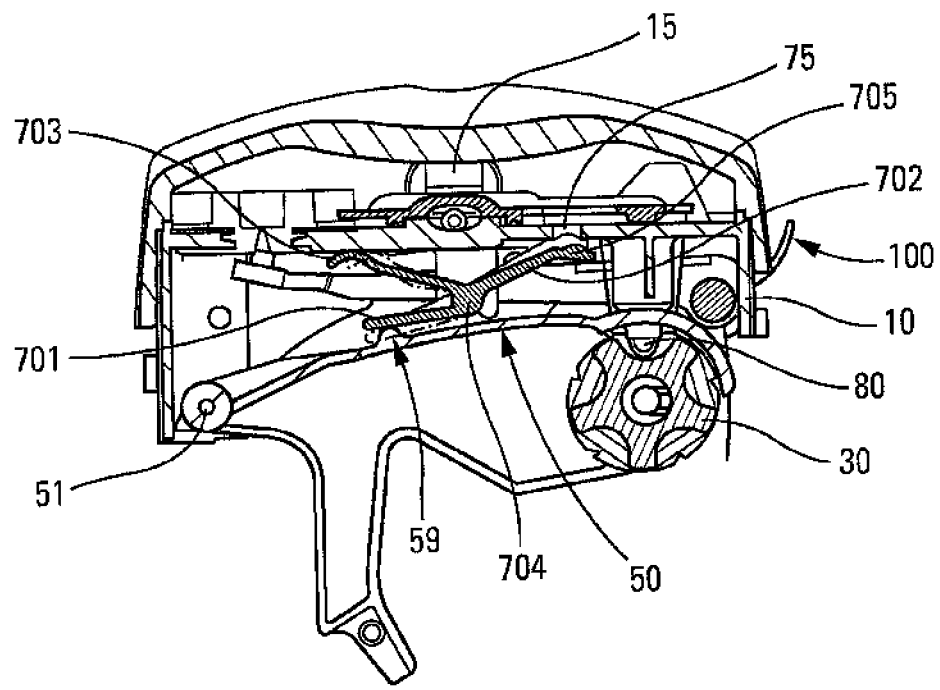
FIG. 3 is a view similar to the view in FIG. 2, shown after inhalation.

Naturally, the invention is not limited to the movable element shown in FIGS. 2 and 3, particularly adapted to the trigger system shown, and the means for modifying the inhalation flow could be different to those shown.

In general, the blister strip is formed by a strip presenting two ends. In a variant, it is possible to use a continuous strip. Other modifications are also possible without going beyond the ambit of the present invention.

The present invention therefore makes it possible to provide a dry-powder inhaler that performs the following functions:

a plurality of individual doses of powder stored in individual sealed reservoirs, e.g. 30 or 60 doses stored on a rolled-up strip;

the powder is released by perforation that is achieved by the user inhaling, the blister being perforated by means of an inhalation detector system that is coupled to a prestressed release system;

appropriately-shaped drive means that are engaged with blisters so as to displace the blister strip on each actuation, and to bring a new reservoir into a position in which it is to be opened by appropriate opening means;

means for avoiding doses being lost in the event of the inhaler being opened, but in the absence of any inhalation. In this event, when the inhaler closes, the device returns exactly to its start position.

Other functions are also provided by the device of the invention as described above. It should be observed that the various functions, even if they are shown as being provided simultaneously on the various embodiments of the inhaler, could be implemented separately. In particular, the inhalation trigger mechanism could be used regardless of the type of reservoir opening means, regardless of the way in which the individual reservoirs are arranged relative to one another, etc. The cocking means and the inhalation trigger system could be made in some other way. The same applies for other component parts of the device.

The inhaler of the invention, incorporating all or some of the above-described functions, provides performance that is superior to the performance of existing devices. In particular, the inhaler of the invention preferably provides a reservoir emptying factor of at least 90% on each actuation. The emptying factor, corresponding to the percentage of fluid that is expelled from an open reservoir while the device is being actuated, is advantageously greater than 95%, preferably even greater than 97%. In particular, this high emptying factor is even greater than the performance obtained with active inhalers that are generally more effective than passive inhalers, and in which it is not the inhalation flow that empties the blister and expels the dose but a flow of compressed air that is released while inhaling. The high emptying factor guarantees that the device of the invention is as effective as possible. Coupled with the inhalation-triggered opening, the high emptying factor guarantees that the fluid, specifically the powder, is dispensed in optimum manner into the user's lungs. The invention also provides improved emptying regularity of the reservoirs during successive actuations. Thus, for ten reservoirs of a blister strip, for example, it turns out that the emptying factor varies by less than 15%, advantageously by less than 10%, preferably by less than 5% from one reservoir to another. This improved regularity guarantees improved dose reproducibility, and therefore also improved effectiveness of the device of the invention.

Various modifications can also be envisaged by a person skilled in the art, without going beyond the ambit of the present invention, as defined by the accompanying claims.

The invention claimed is:

1. A fluid dispenser device comprising:
   a body provided with a dispenser orifice;
   at least one reservoir containing a dose of fluid;
   movable support means that receive at least one reservoir, and that are displaceable between a non-dispensing position and a dispensing position;
   reservoir-opening means for opening a reservoir when said reservoir-opening means are actuated;
   stressing means for urging said movable support means towards said dispensing position, said stressing means including an elastically-deformable spring;
   blocking means for retaining said movable support means in the non-dispensing position corresponding to a cocked position of said blocking means, said blocking means comprising a blocking element connected to a rod;
   inhalation trigger means for releasing said blocking means and for enabling said movable support means, together with a reservoir, to be displaced towards said dispensing position at the time a user inhales, said inhalation trigger means comprising a deformable air chamber or pouch connected to said rod of said blocking means;
   means for modifying an inhalation flow of the user, which, at the start of inhalation, are adapted to use the inhalation flow mainly to actuate said inhalation trigger means, and, at the end of inhalation, are adapted to use the inhalation flow mainly to expel the dose of fluid contained in the reservoir,
   wherein said means for modifying the inhalation flow comprise a movable element that is deformable and/or displaceable between a plugging position in which it plugs an inhalation air passage, and an unplugging position in which it does not plug said inhalation air passage, said movable element being in its plugging position when the movable support means are in the non-dispensing position, and in its unplugging position when the movable support means are in the dispensing position,
   wherein said movable element includes at least two branches that are connected to a pivot-forming central zone, a first branch co-operating with the movable support means, and a second branch co-operating in said plugging position with said inhalation air passage.

2. A device according to claim 1, wherein said movable element includes a third branch that is adapted to bear and/or to slide against a portion that is fixed relative to said body.

3. A device according to claim 1, wherein said blocking element is pivotally mounted on the body.

4. A device according to claim 1, wherein the inhalation of the user generates an inhalation rate of the user lying in the range 10 L/min to 20 L/min in order to release said blocking means.

5. A device according to claim 1, wherein the inhalation of the user generates a pressure difference lying in the range 4 mbar to 15 mbar in order to release said blocking means.

6. A device according to claim 1, including at least one cover element that is movable between a closed position and an open position, the displacement of said at least one movable cover element towards its open position bringing said device into its cocked position.

7. A device according to claim 1, including a plurality of individual reservoirs disposed one behind another on an elongate flexible strip.

8. A device according to claim 1, wherein said reservoir-opening means comprise a perforator needle that is stationary relative to the body.

9. A device according to claim 1, wherein said movable element is elastically deformable relative to said body.

* * * * *